United States Patent [19]

Richalley et al.

[11] Patent Number: 4,844,810

[45] Date of Patent: Jul. 4, 1989

[54] INSTALLATION WITH MULTIPLE FUNCTIONS FOR REPLACEMENT OF THE NATURAL FILTRATION OF THE BLOOD

[75] Inventors: Gerard Richalley, Lyons; Marc Delaunay, Decines, both of France

[73] Assignee: Hospal Industrie, France

[21] Appl. No.: 82,499

[22] Filed: Aug. 7, 1987

[30] Foreign Application Priority Data

Aug. 8, 1986 [FR] France ............................ 86 11663

[51] Int. Cl.⁴ ............................................ B01D 13/00
[52] U.S. Cl. ............................... 210/646; 210/321.72; 210/424; 210/433.1; 210/650; 604/5
[58] Field of Search ...................... 210/321.72–321.81, 210/416.1, 433.1, 418, 420, 424, 428, 646, 647, 650, 651, 652, 653, 654, 655; 604/4, 5, 6

[56] References Cited

U.S. PATENT DOCUMENTS 4,617,115 10/1986 Vantard ........................ 210/321.77

Primary Examiner—W. Gary Jones
Attorney, Agent, or Firm—Finnegan, Henderson, Farabow, Garrett & Dunner

[57] ABSTRACT

An installation having interchangeable functions for the replacement of the natural filtration of the blood. The installation has a reservoir of a sterile physiological solution. A three-way valve is provided in communication with an outlet of the reservoir. By selective adjustment of the three-way valve, the physiological solution from the reservoir may be selectively conveying to a first compartment of an exchanger for the spontaneous or assisted blood circulation and a second compartment for spontaneous or assisted circulation of a dialysis liquid and/or of an ultrafiltrate. A hydraulic resistor is provided for adjusting the circulation conditions of the physiological solution.

18 Claims, 5 Drawing Sheets

INSTALLATION WITH MULTIPLE FUNCTIONS FOR REPLACEMENT OF THE NATURAL FILTRATION OF THE BLOOD

BACKGROUND OF THE INVENTION

1. Field of the Invention:

The present invention comes within the technical sphere of renal insufficiency and relates to replacement equipment used for the extracorporeal filtration of the blood in the case of acute temporary deficiencies or chronic deficiencies.

2. Description of the Prior Art:

There are many prior art practices for performing this replacement function.

A first method uses an exchanger, which is an apparatus divided into two compartments by a semi-permeable membrane. One of the compartments is connected to the patient by extracorporeal blood circulation lines, and the second compartment is connected to a circulation line for the ultrafiltrate extracted from the blood which is collected in a collecting bag provided for this purpose.

An installation of this type can cause spontaneous or assisted blood circulation to take place. The operating principle of such an installation is based on a convection phenomenon employing differential pressures to allow excess water to be extracted and eliminated from the blood.

This method is known as continuous ultrafiltration. It is particularly suitable for a rapid elimination of excess water and simultaneously allows a limited elimination of the metabolic waste products drained by the extracted ultrafiltrate.

Such a method is particularly suitable for the treatment of acute cases where the primary concern is to restore the patient to an acceptable weight by the elimination of excess water.

Such a method is, on the other hand, not suitably adapted to the elimination of the metabolic waste products. The purification of the blood is, in fact, limited by the quantity of ultrafiltrate which can be extracted from the blood.

Another practice, which is termed continuous haemofiltration, uses an installation identical to that described above which is, however, completed by the connection of a spontaneous or assisted line infusing a physiologically sterile, pyrogen free solution into the extracorporeal blood circulation line which is thereby added to the blood to offset the quantity of ultrafiltrate extracted, except for the loss of weight.

Again, this practice employs the convection phenomenon to cause a pressure differential, but the supply of the physiological solution makes it possible to obtain a substantially greater extraction of the metabolic waste products by making provision for longer treatment times.

It will be understood that, because of the infusion of a physiological solution, such a method may not be appropriate in the initial treatment stage in some acute cases where the priority object is a rapid restoration of the patient's normal weight. This is the reason why, in practice, such a method is frequently substituted for the first method after the latter has made it possible to achieve the priority object, and it is then necessary to ensure that the elimination of the metabolic waste products is really obtained.

A third method, known as continuous haemodialysis, is performed by connecting the inlet of the second compartment of the exchanger of the installation to a reservoir for a physiological solution which is caused to circulate in the second compartment, generally in contraflow with the blood circulation, while maintaining the pressure relationship and flow rate relationship with respect to the blood circulation conditions.

The main flow rate relationship is established to create conditions for diffusion through the semi-permeable membrane in the blood compartment-physiological liquid compartment direction. Moreover, the effect of the pressure relationship is to create a transfer by convection from the blood compartment toward the physiological liquid compartment. By this means, it becomes possible to improve the extraction of the metabolic waste products by means of the circulation of the physiological liquid, and more particularly the elimination of small molecules, such as urea.

This method also has a potential for more effective treatment, because it allows better purification of the blood according to commonly accepted criteria.

It may be seen, therefore, that the three known methods per se have, in the sequence in which they are discussed above, a decreasing efficiency for eliminating excess water and increasing efficiency for elimination of the metabolic waste products.

Clinically, it is frequently found that in acute cases the trends in the behavior of the deficient organism require recourse to a treatment method different from the one being applied.

Thus, after a stage of treatment by a continuous ultrafiltration method with a view to restoring normal weight, recourse is frequently made to the continuous haemodialysis. However, with the application of one or the other of the methods, one can sometimes find a fresh solution of water which again has to be rapidly eliminated by recourse to the first method.

Moreover, during a stage of treatment by continuous haemofiltration, it is possible to find modifications of the patient's catabolism, requiring a more effective purification of the blood which, in certain cases, can only be effected by application of the continuous haemodialysis method.

The practitioners are therefore confronted with the problem of frequent change from one installation to another to meet developments in a particular clinical case during the course of treatment.

At the present time, recourse to one or the other of the methods necessarily entails the use of an installation which is appropriate to the method in question and setting up each time the connection of such an installation in communication with the patient to be treated by the appropriate practice. This is not satisfactory, because it represents a considerable constraint for the staff charged with the follow-up of the clinical case to be treated, a significant source of errors with respect to the connections and/or of the relationships of the pressure and flow rates, and requires that a considerable number of installations be provided in reserve. These reserve installations are required because each installation once having been used as a specific connection cannot be modified without incurring the risk of infection.

Thus, there is a need for an installation that allows the practitioner to have the capability for applying one of the three methods in the course of treatment, with the option of changing to another if the priority objective is loss of weight rather than an average or high elimination of the waste products, or vice versa.

SUMMARY OF THE INVENTION

It is accordingly an object of the present invention to provide an installation designed to allow the use of any one of the three replacement methods in an interchangeable manner and requiring only a single manipulation for changing from one method to another.

Another object of the invention is to provide an installation having a connection to a patient that allows recourse to any one of the treatment methods with provision for switching to the desired method according to the selected priority objective to be attained.

Yet another object of the invention is to provide an installation of this type that is of inexpensive, simple structure and yet provides for effective, reliable operation.

Yet another object of the invention is to provide an installation which allows use of a fourth method, if required by the operator, which includes the simultaneous application of a method of continuous haemofiltration and of continuous haemodialysis, termed continuous haemodiafiltration.

Another object of the invention is to provide an installation which could, in spite of its single use character, be easily adapted for establishing a spontaneous or assisted extracorporeal blood circulation and/or a spontaneous physiological solution by means of gravity or applied force, and/or an extraction of the ultrafiltrate and/or of the dialysis liquid, which function may also be either spontaneous or assisted.

The installation with interchangeable functions for the replacement of the natural filtration of the blood in accordance with the invention comprises an exchanger having on opposite sides of a semipermeable membrane a first compartment for the spontaneous or assisted blood circulation and a second compartment for the spontaneous or assisted circulation of a dialysis liquid and/or of an ultrafiltrate. A bag is provided for receiving the dialysis liquid and/or the ultrafiltrate. Means are provided for connecting an inlet and means are provided for connecting an outlet of this first compartment to a patient. Means are also provided for connecting an outlet of the second compartment to the bag. A reservoir of a sterile physiological solution is provided. A three-way valve is in communication with an outlet of the reservoir. Means respectively are provided for conveying the physiological solution to the inlet of the second compartment of the exchanger and to one of the inlet connecting means and outlet connecting means for connecting the first compartment to the patient. The circulating conditions of the physiological solution are adjusted by a hydraulic resistor.

The hydraulic resistor may be static or dynamic and, if dynamic, may be a pump.

The hydraulic resistor may be positioned between the three-way valve and the reservoir.

A pump may be provided for extraction of the dialysis liquid and/or the ultrafiltrate.

A pump may also be provided in communication with the three-way valve for regulating the physiological solution from the reservoir to the means for connecting the outlet of the first compartment of the exchanger to the patient.

A pump may also be provided in communication with the three-way valve and the means for conveying the physiological solution to the inlet of the second compartment.

BRIEF DESCRIPTION OF THE DRAWINGS

The accompanying drawings, which are incorporated in and constitute a part of this specification, illustrate embodiments of the invention and, together with the description, serve to explain the principles and advantages of the invention.

DETAILED DESCRIPTION OF THE PREFERRED EMBODIMENTS

Reference will now be made in detail to presently preferred embodiments of the invention, examples of which are described below and illustrated in the accompanying drawings.

Figure 1:
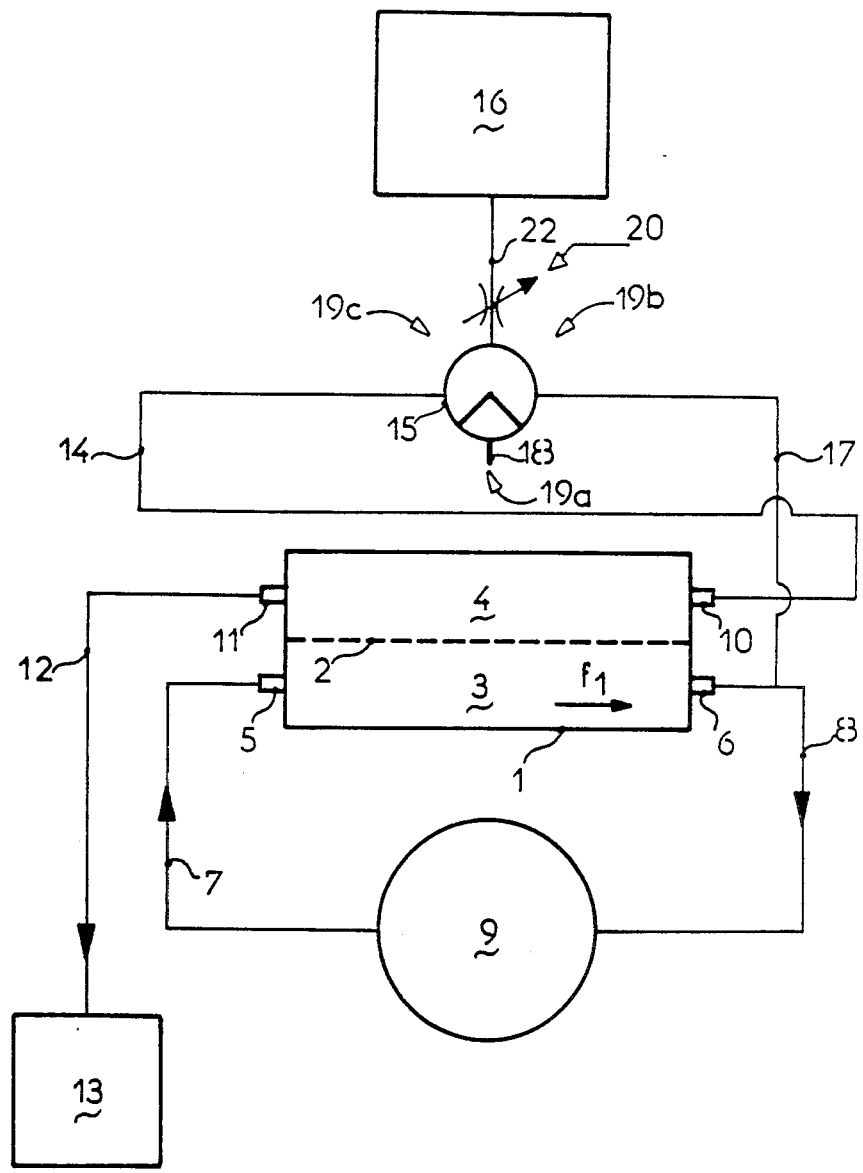
FIG. 1 is a schematic showing of one embodiment of the invention.

FIG. 1 schematically shows an installation with interchangeable functions for the replacement of the natural filtration of the blood in accordance with one embodiment of the invention. This installation comprises an exchanger 1 having characteristics that are chosen to allow random use of one or the other of the three known treatment methods. This exchanger must have the properties of a haemodialyser and those of a haemofilter at one and the same time. The BIOSPAL SCU-CAVH exchanger sold by the HOSPAL Company is very suitable. The exchanger comprises internally a membrane 2 defining two circulation compartments 3 and 4.

The compartment 3, reserved for the blood circulation, has an inlet tube 5 and an outlet tube 6 allowing connection to a patient 9 by the lines 7 and 8, respectively.

The compartment 4 has an inlet tube 10 and an outlet tube 11. The tube 11 is connected by a line 12 to a receiving and collecting bag 13 for the dialysis liquid and/or the ultrafiltrate.

The tube 10 is connected to a line 14 from one of the outlets of a three way valve 15 which in turn is connected via line 22 to the outlet of a reservoir 16 containing a sterile and preferably pyrogen free physiological solution. The second outlet of the three way valve 15 is connected to a line 17 which is in turn connected to the outlet line 8 or alternately to the inlet line 7 of the blood compartment 3 of the exchanger 1. The three way valve 15 has a pointer 18 adapted for selective registration with any one of three marks 19a, 19b and 19c, associated with indicia in plain or symbolic language corresponding, as far as the staff charged with the operation and supervision of such an installation is concerned, to one of the three known replacement methods. The mark 19a can, for instance, correspond to the operation of a method of continuous ultrafiltration, the mark 19b to a continuous haemofiltration method and the mark 19c to a continuous haemodialysis method.

The installation is, moreover, completed by a hydraulic resistor 20, which may be for example, an adjustable clamp or a cock to adjust the flow rate and thus change the circulation conditions of the physiological solution.

The installation described above functions as follows:

In the condition shown in FIG. 1, the three way valve 15 is adjusted with the pointer 18 in registration with mark 19a and thus closes the inlets of lines 14 and 17.

When the extracorporeal blood circulation is established in the direction of the arrows in lines 7, 8 and 12, the blood from patient 9 circulates within the compartment 3 in the direction of the arrow $f_1$. This makes it possible to eliminate the excess water by convection through the membrane 2. The water is evacuated by the line 12 to the collecting bag 13.

The installation in accordance with the invention thus allows a treatment method to be set up by continuous ultrafiltration.

When the three way valve 15 is manipulated to place the pointer 18 in register with mark 19b (FIG. 2), the line 17 communicates with the reservoir 16. When this reservoir is placed in a charging position in relation to the patient 9, a circulation by gravity is established, and the physiological solution contained in the reservoir 16 passes through the three way valve 15 and follows the line 17 for infusion in line 8. In this manner, a post-dilution of the blood is obtained. If desired, the physiological liquid may also be introduced into the line 7 at the inlet of the exchanger 1 to achieve predilution of the blood.

The hydraulic resistor 20 makes it possible to vary the flow rate of the sterile physiological solution. In this manner, the pressure at the head of the reservoir 16 may be a value compatible with that of the blood to allow the physiological solution to be infused in the extracorporeal blood circulation circuit.

In this case, one is concerned with the application of the haemofiltration method, since a charge of the physiological solution is required to follow the extracorporeal blood circulation circuit to promote the elimination of the waste products which are taken up by convection during the passing of the blood within the compartment 3.

Apart from checking that the bag 13 has a suitable head, passing from the first to the second method is achieved solely by positioning of the three way valve 15, which may be manipulated without risk of error, so that the pointer 18 is aligned with the predetermined position corresponding to the method desired.

When the three way valve 15 is manipulated so that its pointer is placed in alignment with the mark 19c (FIG. 3), the physiological solution of the reservoir 16 passes through the hydraulic resistor 20 and into the line 14. This solution is thus caused to pass through the compartment 4 in the direction of the arrow $f_2$ and to effect by diffusion the continuous haemodialysis of the blood circulating in the compartment 3.

The hydraulic resistor 20 allows the flow rate of the physiological solution to be adjusted to create the required condition for the diffusion between the blood and the sterile physiological solution. The height of the reservoir 16 for the sterile physiological solution is adjusted to allow the sterile physiological solution to circulate in the compartment 4 of the exchanger without impeding the blood circulation in the other compartment.

Figure 2:
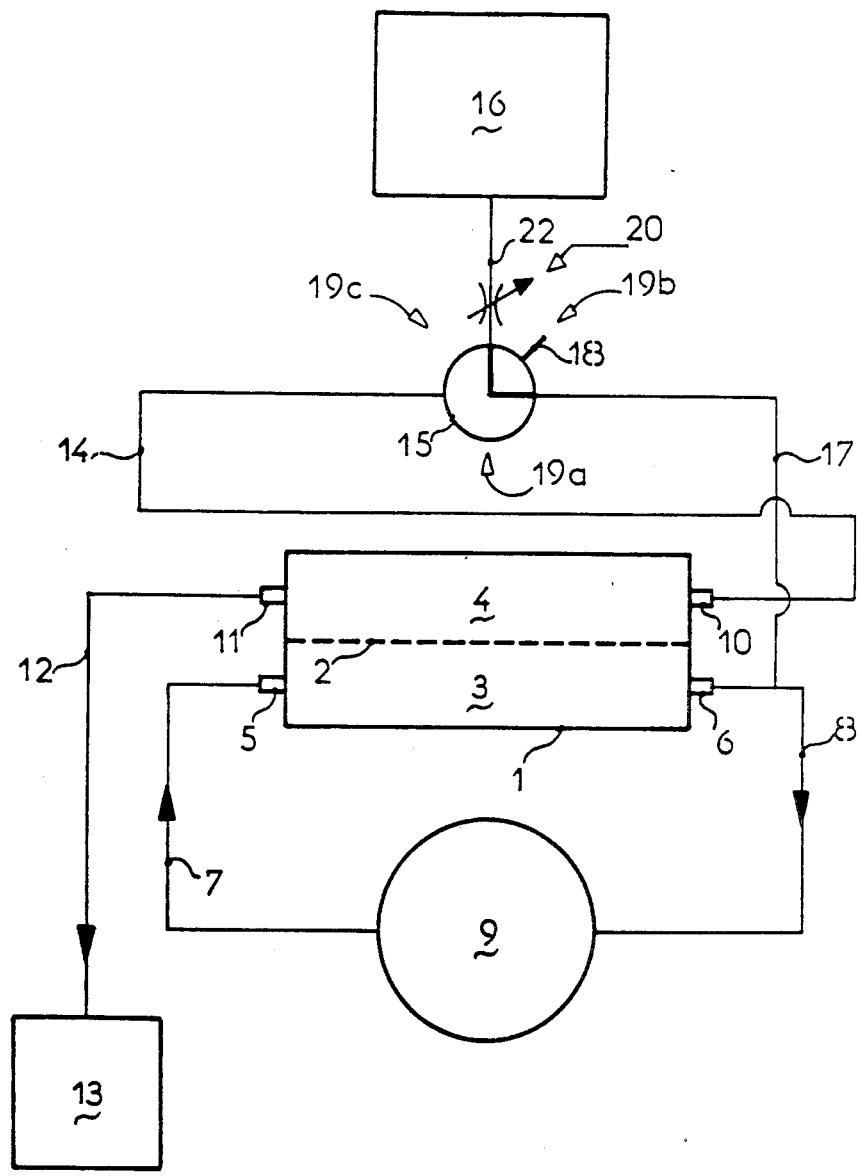
FIG. 2 is a schematic showing of the embodiment of the invention shown in FIG. 1 operating according to a continuous haemofiltration method.
Figure 3:
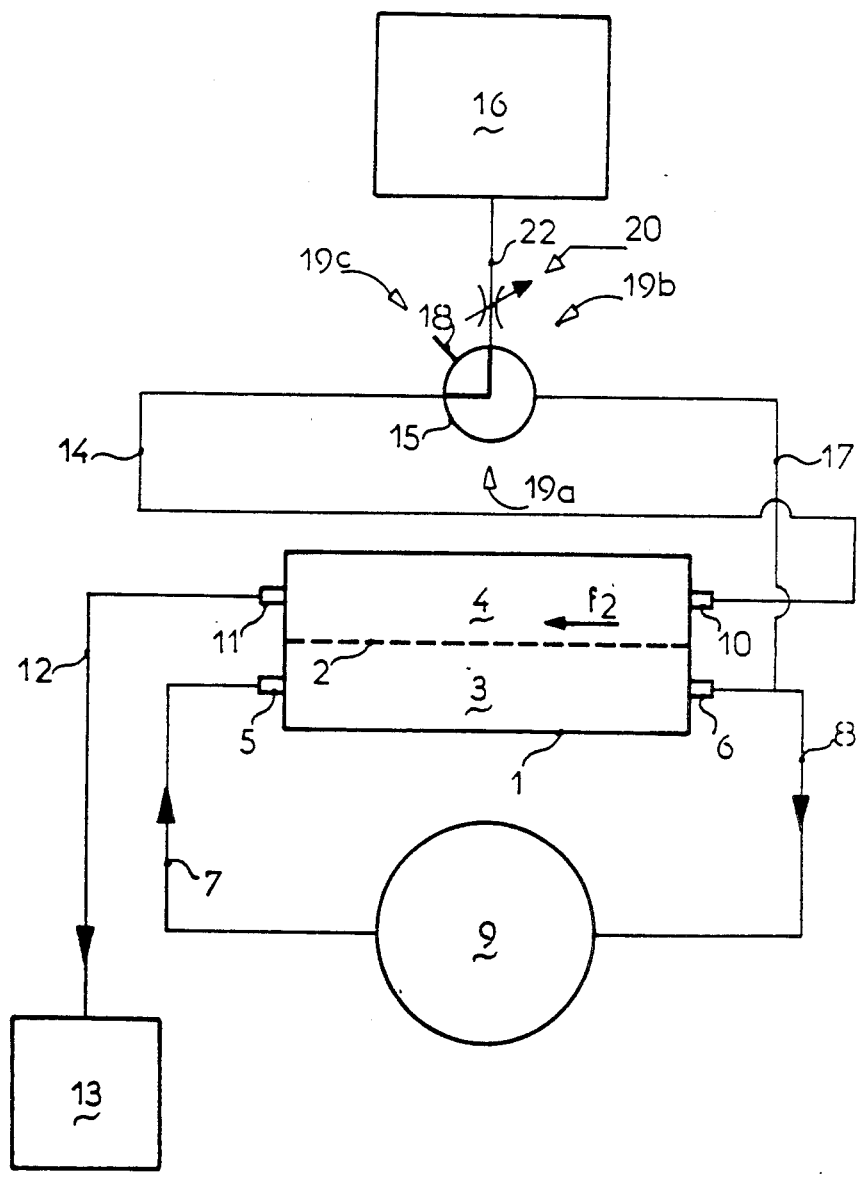
FIG. 3 is a schematic showing of the embodiment of the invention shown in FIG. 1 operating according to a continuous haemodialysis method.

As is shown by a comparison of FIGS. 1, 2 and 3, the simple and reliable manipulation of the three way valve 15 makes it possible to implement by means of one and the same installation, the application of a method of continuous ultrafiltration, continuous haemofiltration or continuous haemodialysis, without any risk of error or improper interpretation, disconnection or reconnection of the installation.

It thus becomes possible to meet the desired object by a simple practice that makes it feasible to offer any practitioner the possibility of having recourse by means of one and the same installation to the implementation of any one of the replacement methods, depending on his diagnosis of the progress of the treatment.

The installation described above can be made, like any one of the known installations, in a simple and inexpensive manner, taking into consideration the single use to which it is put. This results from the possibility of choosing an inexpensive three way valve 15 and hydraulic resistor 20 from the known state of the art, and yet have components capable of reliable operation. Although the first function ensured by the three way valve 15 is the selectivity of the circulation of the sterile physiological solution, it must also have excellent sealing characteristics.

Figure 4:
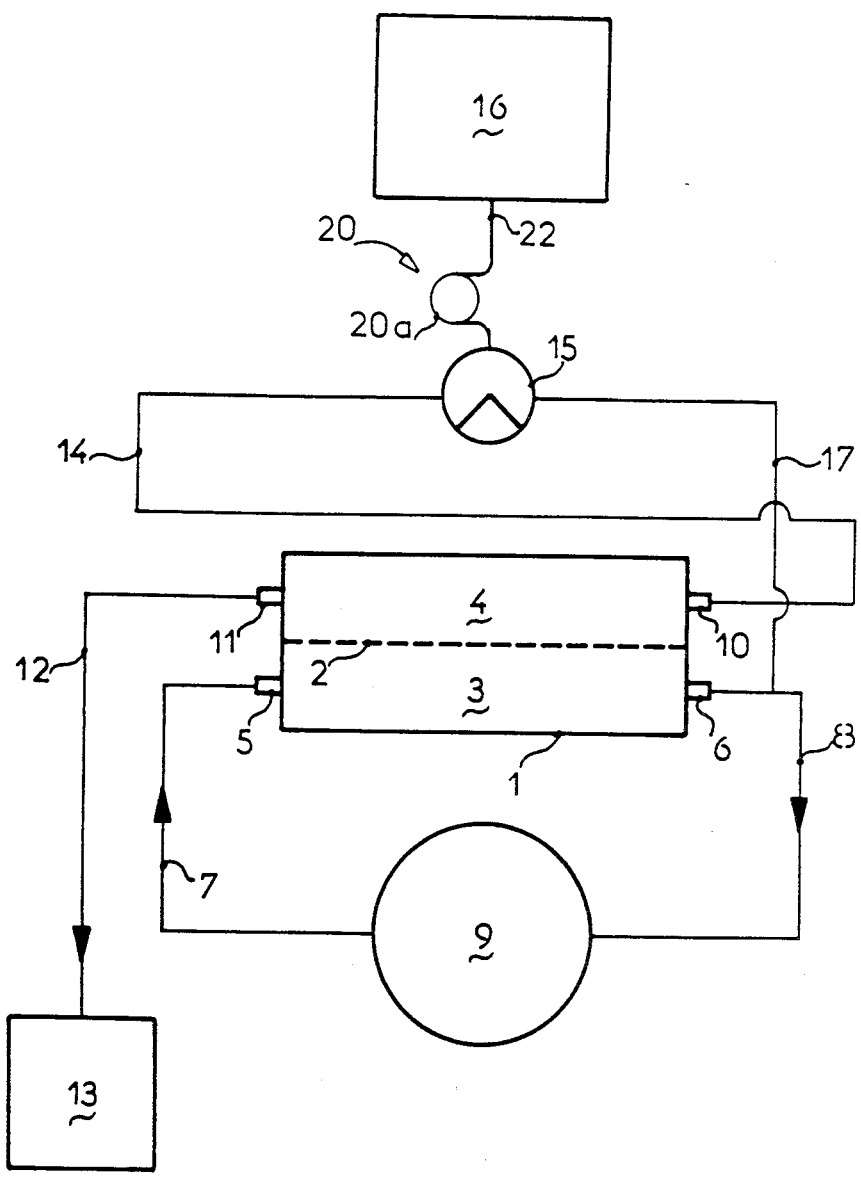
FIG. 4 is a schematic showing of a second embodiment of the invention.

FIG. 4 shows use not of a hydraulic resistor of a static nature as in the example according to FIG. 1, but instead of a hydraulic resistor of a dynamic nature. This consists of, for example, a pump 20a having operating conditions that can be adjusted by an operator to supply a physiological solution having circulation conditions that are compatible with establishing a treatment method by continuous haemofiltration or by continuous haemodialysis.

Figure 5:
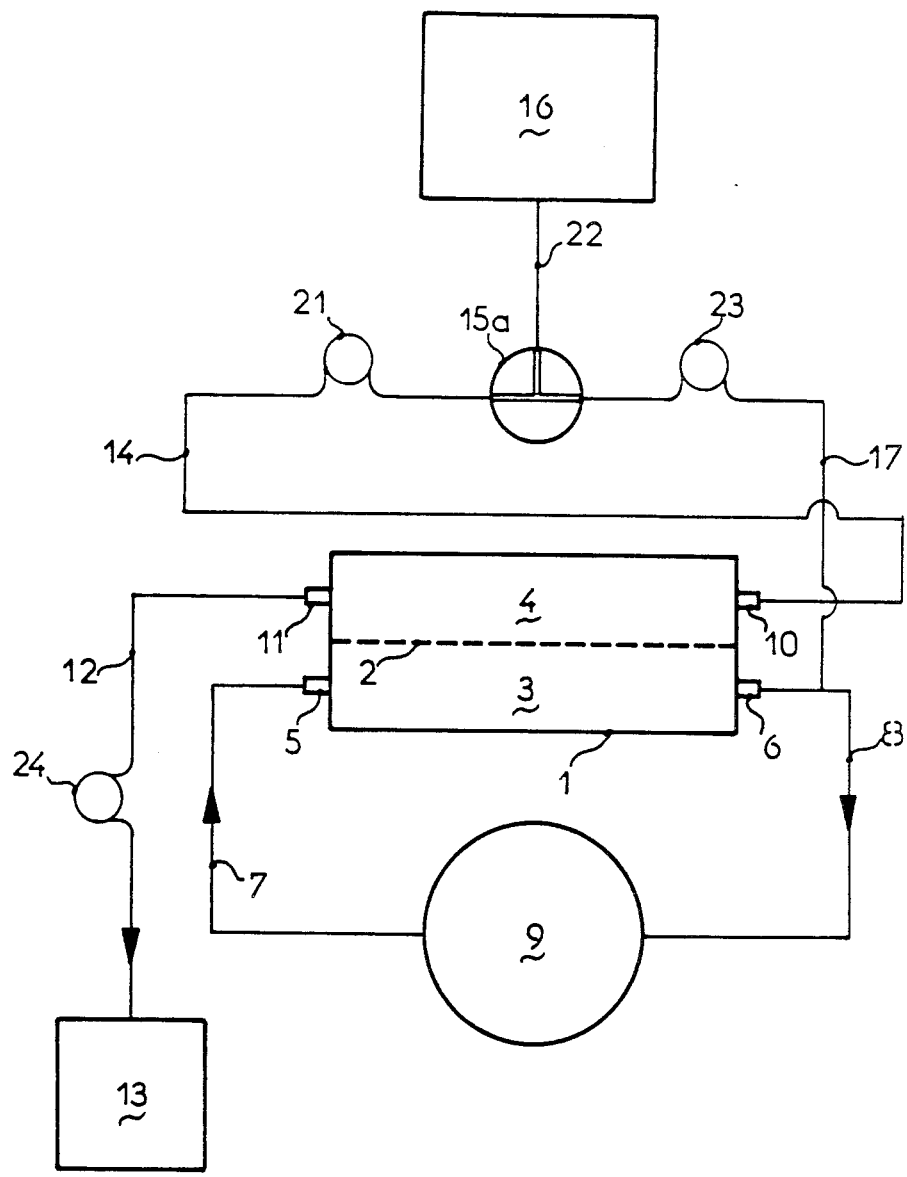
FIG. 5 is a schematic showing of a third embodiment of the present invention.

In the embodiment shown in FIG. 5, it is possible to obtain simultaneously a continuous haemodialysis and haemofiltration (a technique also termed continuous haemodiafiltration). For this purpose, a four-position three-way valve means cock 15a is used having a casing provided with a T-duct allowing the reservoir 16 to be simultaneously connected to the line 14 for the circulation of the physiological liquid serving as the dialysis liquid and the line 17 for the infusion of the physiological liquid into the extracorporeal blood circulation.

FIG. 5 shows that the installation may comprise, apart from the pump 20a (not shown), a pump 24 for assisting the extraction of the dialysis liquid and of the ultrafiltrate. Moreover, the circulation conditions of the physiological solution in the lines 14 and 17 may be regulated by clamps or more advantageously by pumps 21 and 23.

The pumps 20a, 21, 23 and 24 are preferably of the peristaltic type.

The invention is not limited to the described and represented examples because various modifications can be made thereto without departing from its scope.

What is claimed is:

1. A method for the replacement of the natural filtration of a patient's blood utilizing an exchanger defined by a housing and divided into first and second compartments by a semi-permeable membrane, said first compartment being extracorporeally connected to the patient and having an inlet and an outlet for circulating the patient's blood therethrough, said second compartment having an inlet for receiving a sterile physiological solution from a reservoir, and an outlet for discharging fluid from said second compartment to a bag, said reservoir being selectively flow connected through conduit line means to said inlet of said second compartment and to one of said inlet and outlet of said first compartment via a three-way valve disposed in said conduit line means, the method comprising the step of:

selectively setting said three-way valve to one of three operable positions wherein a first position said reservoir is in flow communication with the inlet of said second compartment to perform haemodialysis of the patient's blood, and in a second position said reservoir is in flow communication with one of the said inlet and outlet of said first compartment to perform haemofiltration of the patient's blood, and in a third position said reservoir is isolated from said first and second compartments to perform ultrafiltration of the patient's blood.

2. A method for the replacement of the natural filtration of a patient's blood utilizing an exchanger defined by a housing and divided into first and second compartments by a semi-permeable membrane, said first compartment being extracorporeally connected to the patient and having an inlet and an outlet for circulating the patient's blood therethrough, said second compartment having an inlet for receiving a sterile physiological solution from a reservoir, and an outlet for discharging fluid from said second compartment to a bag, said reservoir being flow connected through conduit line means to selected ones of said inlet of the second compartment and said inlet and outlet of said first compartment via a three-way valve having four operable position settings disposed in said conduit line, the method comprising the step of:

selectively setting said three-way valve to one of said four operable positions wherein in a first position said reservoir is in flow communication with the inlet of said second compartment to perform haemodialysis of the patient's blood, and in a second position said reservoir is in flow communication with one of said inlet and outlet of said first compartment to perform haemofiltration of the patient's blood, and in a third position said reservoir is isolated from said first and second compartments to perform ultrafiltration of the patient's blood, and in a fourth position said reservoir is in flow communication with both said inlet of said second compartment and said one of the inlet and outlet of said first compartment to perform haemodiafiltration of the patient's blood.

3. An installation with interchangeable functions for the replacement of the natural filtration of the blood, comprising:

an exchanger defined by a housing;
a semipermeable membrane disposed in said housing to separate said exchanger into a first compartment for the spontaneous or assisted blood circulation, and a second compartment for spontaneous or assisted circulation of one of a dialysis liquid, an ultrafiltrate, and a combination of dialysis liquid and ultrafiltrate;
a bag for receiving the one of said dialysis liquid, said ultrafiltrate, and said combination of dialysis liquid and ultrafiltrate circulating through said second compartment;
means for defining an inlet and an outlet of said first compartment and for connecting said inlet and said outlet of said first compartment to a patient;
means for defining an inlet and an outlet of said second compartment and for connecting said outlet of said second compartment to said bag;
reservoir means for holding a sterile physiological solution, said reservoir means having an outlet tube extending therefrom;
first conduit line means for flow communicating said outlet tube of said reservoir means and said inlet of said second compartment;
second conduit line means for flow communicating said outlet tube of said reservoir means to one of said inlet and said outlet of said first compartment;
three-way valve means, operable between three setting positions and disposed between said outlet tube of said reservoir and said first and second conduit line means, for selectively passing said sterile physiological solution from said reservoir means through one of said first and second conduit line means and for isolating said reservoir means from both said first and second conduit line means in accordance with the respective operable setting positions of said three-way valve means; and
hydraulic resistor means for adjusting circulation conditions of said physiological solution.

4. An installation according to claim 3, wherein said hydraulic resistor is static.

5. An installation according to claim 3, wherein said hydraulic resistor is dynamic.

6. An installation according to claim 3 or claim 4 or claim 5, wherein said hydraulic resistor is positioned between said three-way valve and said reservoir.

7. An installation according to claim 3 or claim 5 wherein said hydraulic resistor is a pump.

8. An installation according to claim 3, wherein a first pump is provided for the extraction of said one of the dialysis liquid, the ultrafiltrate, and the combination of dialysis liquid and ultrafiltrate from said second compartment.

9. An installation according to claim.8, wherein a second pump is provided in communication with said three-way valve means for regulating the flow of said physiological solution through said second conduit line means.

10. An installation according to claim 9, wherein a third pump is provided in communication with said three-way valve and said first conduit line means for conveying said physiological solution to said inlet of said second compartment.

11. An installation according to claim 3, wherein a pump is provided in communication with said three-way valve means for regulating the flow of said physiological solution through said second conduit line means.

12. An installation according to claim 3, wherein a pump is provided in communication with said three-way valve and said first conduit line means for conveying said physiological solution to said inlet of said second compartment.

13. An installation with interchangeable functions for the replacement of the natural filtration of the blood, comprising:

an exchanger defined by a housing;
a semipermeable membrane disposed in said housing to separate said exchanger into a first compartment for the spontaneous or assisted blood circulation, and a second compartment for the spontaneous or assisted circulation of one of a dialysis liquid, an ultrafiltrate, and a combination of dialysis liquid and ultrafiltrate;

a bag for receiving the one of said dialysis liquid, said ultrafiltrate, and said combination of dialysis liquid and ultrafiltrate circulating through said second compartment;

means for defining an inlet and an outlet of said first compartment and for connecting said inlet and said outlet of said first compartment to a patient;

means for defining an inlet and an outlet of said second compartment and for connecting said outlet of said second compartment to said bag;

reservoir means for holding a sterile physiological solution, said reservoir means having an outlet tube extending therefrom;

first conduit line means for flow communicating said outlet tube of said reservoir means and said inlet of said second compartment;

second conduit line means for flow communicating said outlet tube of said reservoir means to one of said inlet and said outlet of said first compartment; and three-way valve means, operable between three setting positions and disposed between said outlet tube of said reservoir and said first and second conduit line means, for selectively passing said sterile physiological solution from said reservoir means through one of said first and second conduit line means and for isolating said reservoir means from both said first and second conduit line means in accordance with the respective operable setting positions of said three-way valve means.

14. An installation with interchangeable functions for the replacement of the natural filtration of the blood, comprising:

an exchanger defined by a housing;

a semipermeable membrane disposed in said housing to separate said exchanger into a first compartment for the spontaneous or assisted blood circulation, and a second compartment for the spontaneous or assisted circulation of one of a dialysis liquid, an ultrafiltrate, and a combination of dialysis liquid and ultrafiltrate;

a bag for receiving the one of the said dialysis liquid, said ultrafiltrate, and said combination of dialysis liquid and ultrafiltrate circulating through said second compartment;

means for defining an inlet and an outlet of said first compartment and for connecting said inlet and said outlet of said first compartment to a patient;

means for defining an inlet and an outlet of said second compartment and for connecting said outlet of said second compartment to said bag;

reservoir means for holding a sterile physiological solution, said reservoir means having an outlet tube extending therefrom;

first conduit line means for flow communicating said outlet tube of said reservoir means and said inlet of said second compartment;

second conduit line means for flow communicating said outlet tube of said reservoir means to one of said inlet and said outlet of said first compartment; and three-way valve means, operable between four setting positions and disposed between said outlet tube of said reservoir and said first and second conduit line means, for selectively passing said sterile physiological solution along one of the following paths corresponding to respective ones of said four setting positions:

(a) from said reservoir means through said first conduit line means;

(b) from said reservoir means through said second conduit line means;

(c) from said reservoir means through both said first and second conduit line means; and (d) from said reservoir means through said outlet tube and only up to said three-way valve means thereby isolating both said first and second conduit line means from said reservoir.

15. An installation according to claim 14, wherein a first pump is provided for the extraction of said one of the dialysis liquid, the ultrafiltrate, and the combination of dialysis liquid and ultrafiltrate from said second compartment.

16. An installation according to claim 15, wherein a second pump is provided in communication with said three-way valve means for regulating the flow of said physiological solution through said second conduit line means.

17. An installation according to claim 15, wherein a third pump is provided in communication with said three-way valve and said first conduit line means for conveying said physiological solution to said inlet of said second compartment.

18. An installation according to claim 14, wherein a pump is provided in communication with said three-way valve means for regulating the flow of said physiological solution through said second conduit line means.

* * * * *